United States Patent [19]

Hudimac, Jr.

[11] Patent Number: 4,474,175
[45] Date of Patent: Oct. 2, 1984

[54] SAFETY MEANS FOR ADMINISTRATION OF ANESTHETIC GAS

[75] Inventor: George S. Hudimac, Jr., Allentown, Pa.

[73] Assignee: Mechanical Service Company Inc., Allentown, Pa.

[21] Appl. No.: 399,001

[22] Filed: Jul. 16, 1982

[51] Int. Cl.³ .......................................... A61M 16/00
[52] U.S. Cl. .............................. 128/202.22; 340/611; 340/626; 307/118; 307/144; 137/557; 116/70
[58] Field of Search ................... 128/202.22, 205.23, 128/203.12, 204.14; 340/611, 614, 626; 307/118, 144; 137/557; 116/70

[56] References Cited

U.S. PATENT DOCUMENTS

| | | | |
|---|---|---|---|
| 1,675,849 | 7/1928 | Fultz | 137/557 |
| 4,191,952 | 3/1980 | Schreiber et al. | 128/202.22 |
| 4,216,469 | 8/1980 | Hirmann et al. | 116/70 |
| 4,237,813 | 12/1980 | Howison | 137/557 |

FOREIGN PATENT DOCUMENTS 992766  5/1965  United Kingdom ........... 128/205.23

Primary Examiner—Henry J. Recla
Attorney, Agent, or Firm—Frederick J. Olsson

[57] ABSTRACT

A control device in an anesthetic administering system which senses the dangerous condition of nitrous oxide flowing to the patient's breathing mask in the absence of oxygen flow to the mask and provides a warning signal so the condition is known and, thus, is correctable.

4 Claims, 3 Drawing Figures

SAFETY MEANS FOR ADMINISTRATION OF ANESTHETIC GAS

The invention in general relates to hospital operating room anesthetic equipment.

In particular the invention relates to a device to be disposed between the patient's breathing mask and the sources of nitrous oxide and oxygen to sense the condition wherein nitrous oxide is flowing to the breathing mask while oxygen is not so flowing and produce a warning signal so the condition is made known and subject to correction and, thus, avoid severe injury to the patient.

The prime objective and advantage of the invention is to provide for patient safety during a surgical operation.

A typical embodiment of the invention will be described below in connection with the following drawings wherein.

The conventional anesthetic gas comprises nitrous oxide and oxygen, the former being the component rendering the patient insensitive to pain or like sensations. Thus, the anesthetizing component of the gas is described herein as nitrous oxide, it being understood that nitrous oxide is used for explanatory purposes since the invention accomodates other gases that produce anesthesia.

Figure 1:
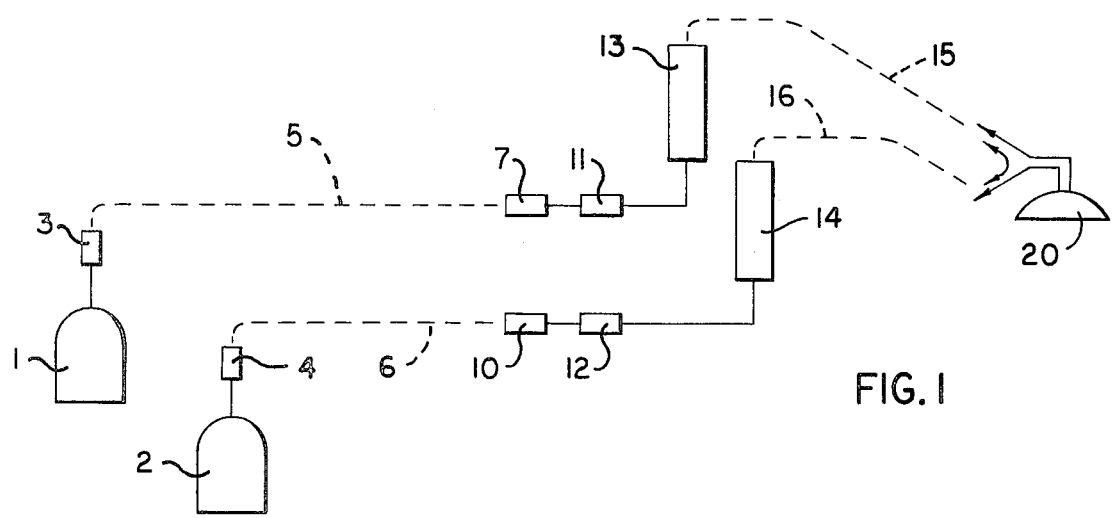
FIG. 1 is a diagramatic view to illustrate the general arrangement of an anesthetic gas administration system conventionally used in hospitals.

In FIG. 1 the tank 1 of nitrous oxide ($N_2O$) and the tank 2 of oxygen ($O_2$) are under high pressure usually in the range of 2,000 psi. Each tank has a pressure regulator/gauge respectively indicated at 3 and 4; these regulators drop the pressure in the order of 50 psi. Flexible lines 5 and 6 connect pressure regulators 3 and 4, pressure regulators 7 and 10, and the flow control valves 11 and 12 to the inputs of the flow meters 13 and 14.

The outputs of the flow meters are respectively connected to the corrugated flexible tubes 15 and 16 both of which are joined to the patient's breathing mask 20 where the gases are mixed and breathed in by the patient.

Once the regulators 3 and 4 are set by the anesthesiologist to obtain the desired low level pressure in lines 5 and 6 (about 50 psi) the pressure regulators 7 and 10 are set to bring the gases within the desired working pressure (about 20-30 psi). The volume of each gas is controlled by the flow control valves 11 and 12.

The desired amount of flow is monitored by the flow meters 13 and 14.

For anesthesizing the patient, the sequence is to activate the oxygen and then follow with the nitrous oxide. Constant introduction of nitrous oxide into the breathing mask without a compatible amount of oxygen can cause severe damage and even death to a patient.

It will be apparent that the above dangerous condition can be brought about simply by the mistake of activating the nitrous oxide without activating the oxygen.

The present invention provides a simple and practical solution to the above problem by that an audible alarm is sounded if the nitrous oxide is turned on prior to the oxygen or more specifically the alarm sounds if there is nitrous oxide flow in the absence of oxygen flow to the patient's mask.

The various components of the control device of the invention are desirable arranged in a cabinet with needed actuating knobs, etc. on the exterior surface. The pneumatic and electrical components employed are of conventional design, per se and, thus, for present purposes the invention can be described using illustrations of the kind shown in FIGS. 2 and 3. The cabinet may take a variety of sizes and shapes depending on component size and desired relative location.

The invention may be included as part of an anesthetic system installed as original equipment in a hospital or can be arranged in kit form for use in the after market and incorporated in existing systems. In either case, the invention is adapted to be disposed between system flow meters and the flow control valves for same.

Figure 2:
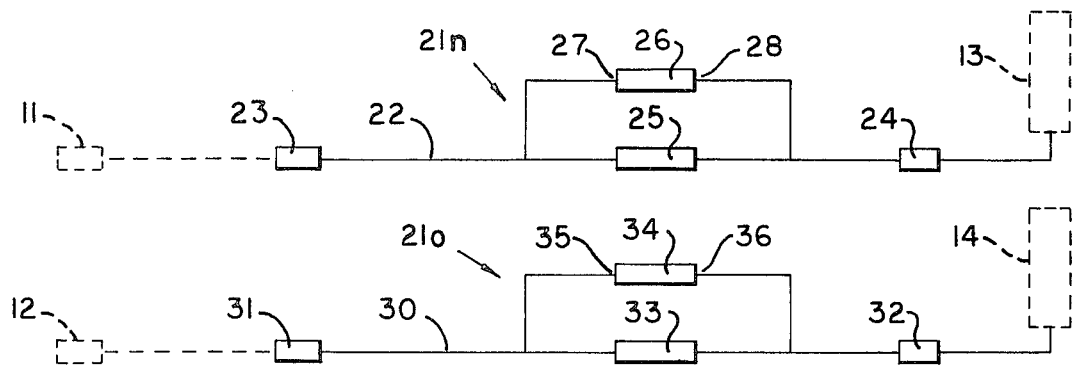
FIG. 2 is a diagramatic view of the invention to be disposed between the patient's breathing mask and the sources of nitrous oxide and oxygen.

Thus, in FIG. 2 the nitrous oxide components 21-n are disposed between the flow control valve 11 and flow meter 13 and the oxygen components 21-o are disposed between the flow control valve 12 and the flow meter 14.

A line 22 has a nitrous oxide inlet connector 23 on one end for connecting the line to flow control valve 11 and, thus, connecting the line 22 to the source 1 of nitrous oxide. The other end of line 22 has a nitrous oxide outlet connector 24 for connecting the line 22 to the nitrous oxide flow meter 13. A flow restrictor 25 is connected in line 22 between the connectors 23 and 24. The restrictor 25 is preferably a fixed or variable orifice needle valve. When nitrous oxide flows in the line 22, a pressure difference develops across the restrictor and this causes the pressure at inlet 27 to be higher than the outlet pressure.

Connected to the line 22 in parallel with the restrictor 25 is a differential pressure sensor 26. The sensor 26 is preferably the diaphram type. When the pressures at the inlet 26 and outlet 27 are equal, the diaphram assumes a neutral position. Pressure on the inlet side 27 which is higher than the pressure on the outlet side 28 will cause the diaphram to move away from neutral. The diaphram is connected to a pin so that diaphram movement causes the pin to move and engage a microswitch arm thereby activating the switch contacts.

As used with the sensor 26, the microswitch contacts are spring biased normally open and are closed by the pin motion as when the diaphram responds to higher inlet pressure. When the inlet and outlet pressure are the same, the diaphram returns to its neutral position causing the pin to position the microswitch arm so that the contacts are opened.

Figure 3:
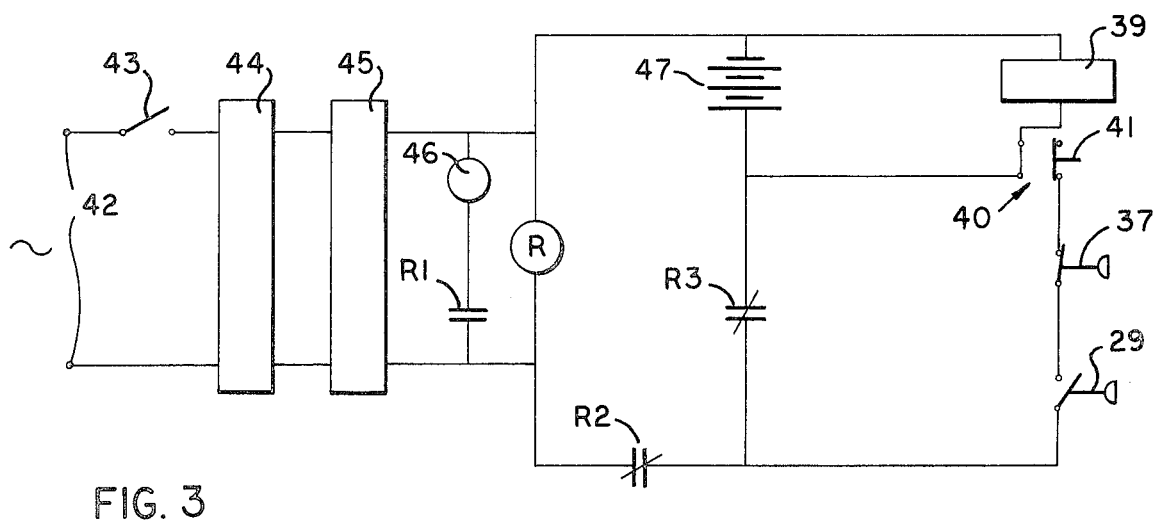
FIG. 3 is a circuit diagram employed with the components of FIG. 2.

The microswitch contacts referred to above are noted at 29 in FIG. 3.

In FIG. 2, the oxygen components 21-o are arranged similarly as the nitrous oxide components 21-n.

The line 30 has an oxygen inlet connector 31 on one end for connecting the line to flow control valve 12 and, thus, connecting the line 30 to the source 2 of oxygen. The other end of line 30 has an oxygen outlet connector 32 for connecting the line to the oxygen flow meter 14. A restrictor 33 is connected in the line 30 between the connectors 31 and 32 and a differential pressure sensor 34 is connected to line 30 in parallel with the restrictor 33. The restrictor 33 and sensor 34 are of the same construction as the restrictor 25 of sensor 26. The microswitch of the sensor 34 has its contact closed when the inlet 35 and outlet 26 pressures are equal. Thus, when the sensor diaphram moves in response to higher pressure at the inlet 35 the normally closed contacts of the microswitch are opened. The microswitch contacts referred to are noted at 37 of FIG. 3.

The contacts 29 and 37 in FIG. 2 control the operation of an electrical alarm 39 which provides an audible signal when nitrous oxide flows into the patient's mask without the simultaneous flow of oxygen. The contacts remain as shown or are opened and closed by the operation of the sensors 26 and 34 as previously noted.

The contacts 29 and 37 and alarm 39 are part of circuit 40 which also includes the manually operated, normally closed test switch 41.

The power means to supply power to the circuit 40 will now be explained.

A conventional 110 volt a.c. source 42 is activated by on-off switch 43 so that the power is supplied to transformer 44 for reducing the voltage to a conventional instrumentation level (about 12 volts) and to a rectifier 45 for obtaining d.c. power.

When the switch 43 is closed the relay R is energized and this closes the contacts $R_1$ and $R_2$ and opens contact $R_3$.

The closing of contact $R_1$ causes energizing of the power-on light 46. The closing of contacts $R_2$ puts the d.c. power across the circuit 40.

It will be noted that with the nitrous oxide contacts 29 open and oxygen contacts 37 closed, the alarm 39 is in the de-energized condition.

If nitrous oxide flows while oxygen is not flowing, the contacts 29 will be closed and the contacts 37 will remain closed and, therefore, the alarm 39 will be energized and so warn of said flow condition. If the oxygen is then made to flow, then the contacts 37 will open and the alarm de-energized.

If for some reason during the operation, the oxygen flow should fail, the contacts 37 will again close and the alarm sound.

The invention contemplates an auxiliary of failsafe source of power which is available to energize the circuit 40 if the main power should fail, for example, a failure of the transformer 44 or rectifier 45. This auxiliary source includes the battery 47 which will feed power to circuit 40 by the opening and closing of relay contacts $R_3$. Thus, for any reason if the power from source 42 fails, the contacts $R_3$ close and power will be available to energize the alarm 39 if needed.

The auxiliary arrangement also includes a test battery tester which includes the push button switch 41. If the switch 41 is depressed, the batteries will cause the alarm 39 to sound. If no alarm sounds, the battery can be replaced.

While the invention has been described in connection with conventional non-solid-state components, it will be understood that the invention can be achieved using solid state technology. Also it will be apparent that the electrical signal generated by the alarm unit 39 to produce audible sound can be employed to trigger a more complex warning and/or correction system such as for example a control to automatically cause the oxygen to flow.

I claim:

1. For a system to administer anesthetic gas of the kind comprising nitrous oxide and oxygen, the system including sources of nitrous oxide and oxygen, a patient's breathing mask, nitrous oxide and oxygen flow meters to respectively monitor the gases flowing to the mask, a gas flow safety warning control to be inserted between the respective sources of nitrous oxide and oxygen and the flow meters comprising:

a first line for conducting nitrous oxide;

nitrous oxide inlet connector means on one end of said first line for connecting the first line to the source of nitrous oxide;

nitrous oxide outlet connector means on the opposite end of said first line for connecting the first line to the nitrous oxide flow meter;

first flow restrictor means in said first line to restrict the flow of nitrous oxide as between the nitrous oxide inlet connector means and the nitrous oxide outlet connector means and create a pressure difference between said nitrous inlet and outlet connector means;

first differential pressure sensing means having a set of normally open electrical contacts, said sensing means being connected to said first line in parallel with said restrictor means and operative upon nitrous oxide flow as between said nitrous oxide inlet and outlet connector means to sense said pressure difference and close said normally open electrical contacts;

a second line for conducting oxygen;

oxygen inlet connector means connected to one end of said second line for connecting the second line to the source of oxygen;

oxygen outlet connector means on the opposite end of said second line for connecting the second line to the oxygen flow meter;

second flow restrictor means in said second line to restrict the flow of oxygen as between the oxygen inlet connector means and the oxygen outlet connector means and create a pressure difference between said oxygen inlet and outlet connector means;

second differential pressure sensing means including a set of normally closed electrical contacts, the sensing means being connected to said second line parallel with said second restrictor means and operative upon oxygen flow as between said oxygen inlet and outlet connector means to sense said pressure difference and open said normally closed electrical contacts;

electrical circuit means including an audio alarm and said normally open and normally closed electrical contacts respectively in series with said audio alarm; and first power means to supply electrical power to said electrical circuit means so that upon closure of said normally open electrical contacts due to flow of nitrous oxide in said first line and the continued closure of said normally closed electrical contacts due to the absence of oxygen flow in said second line causing the energizing of said alarm whereby to provide a warning that nitrous oxide is flowing to the patient's mask in the absence of oxygen flow.

2. The control of claim 1 having fail-safe mechanism comprising:

second power means to supply electrical power to said circuit means; and means connected to said first and to said second power means to:

(a) disconnect said second power means from said electrical circuit means during the time said first power means is supplying power to said electrical circuit means; and (b) connect said second power means to said electrical circuit means in the event said first power means fails to supply power to said electrical circuit means.

3. In a system to administer anesthetic gas of the kind comprising nitrous oxide and oxygen, the system including sources of nitrous oxide and oxygen, a patient's breathing mask, nitrous oxide and oxygen flow meters to respectively monitor the gases flowing to the mask, a gas flow safety warning control to be inserted between the respective sources of nitrous oxide and oxygen and the flow meters comprising:

a first line connected between said source of nitrous oxide and said nitrous oxide flow meter to conduct nitrous oxide therebetween;

first differential pressure having a set of normally open electrical contacts and means connected to said first line to sense the absence of flow of nitrous oxide in said first line and maintain said set of normally open contacts in said open condition and also to sense the flow of nitrous oxide in said first line and cause the closure of said normally open contacts;

a second line connected between said source of oxygen and said oxygen flow meter to conduct oxygen therebetween;

second differential pressure mechanism having a set of normally closed electrical contacts and means connected to said second line to sense the absence of flow of oxygen in said second line and maintain said set of normally closed contacts in said closed condition and also to sense the flow of oxygen in said second line and cause the opening of said normally closed contacts;

electrical circuit means including an audio alarm and said normally open and normally closed electrical contacts respectively in series with said audio alarm;

first power means to supply electrical power to said electrical circuit means so that upon closure of said normally open electrical contacts due to flow of nitrous oxide in said first line and the continued closure of said normally closed electrical contacts due to the absence of oxygen flow in said second line causing the energizing of said alarm whereby to provide a warning that nitrous oxide is flowing to the patient's mask in the absence of oxygen flow.

4. The control of claim 3 having fail-safe mechanism comprising:

second power means to supply electrical power to said circuit means; and means connected to said first and to said second power means to:

(a) disconnect said second power means from said circuit means during the time said first power means is supplying power to said electrical circuit means; and (b) connect said second power means to said electrical circuit means in the event said first power means fails to supply power to said electrical circuit means.

* * * * *